United States Patent
Seese et al.

(10) Patent No.: US 7,163,531 B2
(45) Date of Patent: *Jan. 16, 2007

(54) USER-FRIENDLY CATHETER CONNECTION ADAPTERS FOR OPTIMIZED CONNECTION TO MULTIPLE LUMEN CATHETERS

(75) Inventors: Timothy M. Seese, Palos Hills, IL (US); William Griswold, Bristol, WI (US); Scott Ruddell, Gurnee, IL (US)

(73) Assignees: Baxter International, Inc., Deerfield, IL (US); Baxter Healthcare S.A., Zurich (CH)

( * ) Notice: Subject to any disclaimer, the term of this patent is extended or adjusted under 35 U.S.C. 154(b) by 654 days.

This patent is subject to a terminal disclaimer.

(21) Appl. No.: 10/222,982

(22) Filed: Aug. 19, 2002

(65) Prior Publication Data

US 2004/0034324 A1 Feb. 19, 2004

(51) Int. Cl.
*A61M 25/16* (2006.01)
(52) U.S. Cl. .......................... 604/533; 604/43; 604/246; 604/523
(58) Field of Classification Search ........ 604/533–539, 604/153, 175, 93, 264, 265; 285/12, 417
See application file for complete search history.

(56) References Cited

U.S. PATENT DOCUMENTS

| | | | |
|---|---|---|---|
| 4,581,012 A | * | 4/1986 | Brown et al. .................. 604/43 |
| 4,623,327 A | | 11/1986 | Mahurkar |
| 4,739,768 A | | 4/1988 | Engelson |
| 4,753,640 A | * | 6/1988 | Nichols et al. .............. 604/247 |
| 4,781,185 A | | 11/1988 | Kauphusman et al. |
| 4,842,582 A | | 6/1989 | Mahurkar |
| D303,712 S | | 9/1989 | Goldberg |
| 4,929,236 A | * | 5/1990 | Sampson ..................... 604/175 |
| 4,950,255 A | | 8/1990 | Brown et al. |
| 4,950,259 A | | 8/1990 | Geary et al. |
| 5,009,636 A | | 4/1991 | Wortley et al. |
| 5,053,023 A | | 10/1991 | Martia |
| 5,057,073 A | | 10/1991 | Martin |

(Continued)

FOREIGN PATENT DOCUMENTS

DE  100 42 067 A1  3/2002

(Continued)

*Primary Examiner*—Nicholas D. Lucchesi
*Assistant Examiner*—Aamer S. Ahmed
(74) *Attorney, Agent, or Firm*—Joseph P. Reagen; Bell, Boyd & Lloyd LLC

(57) ABSTRACT

A catheter connection adapter is provided which allows for a user-friendly and mistake-proof connection of a multiple lumen catheter from a dialysis patient to a source of dialysis fluid. The connection adapter contains at least two ports, e.g., one for inflow and one for outflow, and may have a tapered gap between the ports so that an interference fit is made when the ports are inserted into the catheter. In addition, the ports may have a unique key and lock configuration with the catheter such that a fit can only be made when the catheter lumens and the ports are in proper alignment, and the ports may be unconnected to one another so as to provide separate fluid paths for inflow or outflow. The connection adapters are advantageous in that they will allow a multiple lumen catheter to be manually connected to other dialysis equipment following implantation in a patient.

23 Claims, 7 Drawing Sheets

U.S. PATENT DOCUMENTS

| | | |
|---|---|---|
| 5,125,913 A | 6/1992 | Quackenbush |
| 5,129,891 A | 7/1992 | Young |
| 5,156,592 A | 10/1992 | Martin et al. |
| 5,167,623 A | 12/1992 | Cianci et al. |
| 5,188,593 A | 2/1993 | Martin |
| 5,190,529 A | 3/1993 | McCrory et al. |
| 5,221,255 A | 6/1993 | Mahurkar et al. |
| 5,346,471 A | 9/1994 | Raulerson |
| 5,348,536 A | 9/1994 | Young et al. |
| 5,380,276 A | 1/1995 | Miller et al. |
| 5,399,165 A | 3/1995 | Paul, Jr. |
| 5,417,672 A | 5/1995 | Nita et al. |
| 5,451,206 A | 9/1995 | Young |
| 5,456,676 A | 10/1995 | Nelson et al. |
| 5,480,380 A | 1/1996 | Martin |
| 5,486,159 A | 1/1996 | Mahurkar |
| 5,531,723 A | 7/1996 | Solazzo |
| 5,569,182 A | 10/1996 | Twardowski et al. |
| 5,632,729 A * | 5/1997 | Cai et al. ............. 604/288.01 |
| 5,667,490 A | 9/1997 | Keith et al. |
| 5,683,640 A | 11/1997 | Miller et al. |
| 5,743,873 A | 4/1998 | Cai et al. |
| 5,792,124 A | 8/1998 | Horrigan et al. |
| 5,827,237 A | 10/1998 | Macoviak et al. |
| 5,868,717 A | 2/1999 | Prosl |
| 5,961,485 A | 10/1999 | Martin |
| 5,961,486 A | 10/1999 | Twardowski et al. |
| 5,976,103 A | 11/1999 | Martin |
| 6,086,555 A * | 7/2000 | Eliasen et al. ........... 604/93.01 |
| 6,113,572 A * | 9/2000 | Gailey et al. ............ 604/93.01 |
| D431,651 S | 10/2000 | Molina |
| 6,135,992 A | 10/2000 | Wang |
| 6,190,349 B1 | 2/2001 | Ash et al. |
| 6,190,372 B1 | 2/2001 | Racz |
| 6,254,589 B1 | 7/2001 | Raoz |
| 6,875,193 B1 * | 4/2005 | Weisel et al. ................ 604/22 |
| 6,981,977 B1 * | 1/2006 | Herweck et al. ............ 606/153 |

FOREIGN PATENT DOCUMENTS

| | | |
|---|---|---|
| EP | 0 333 308 B1 | 9/1989 |
| EP | 0 553 254 B1 | 8/1993 |
| JP | 1-171499 | 7/1989 |
| JP | 1-303159 | 12/1989 |
| JP | 2-116380 | 5/1990 |
| JP | 8-206216 | 8/1996 |
| JP | 8-269224 | 10/1996 |
| JP | 2000-45999 | 2/2000 |
| WO | WO 96/29111 | 9/1990 |
| WO | WO 91/10456 A1 | 7/1991 |
| WO | WO 92/07215 A1 | 4/1992 |
| WO | WO 94/05363 | 3/1994 |
| WO | WO 96/37254 A3 | 11/1996 |
| WO | WO 02/30489 | 4/2002 |

* cited by examiner

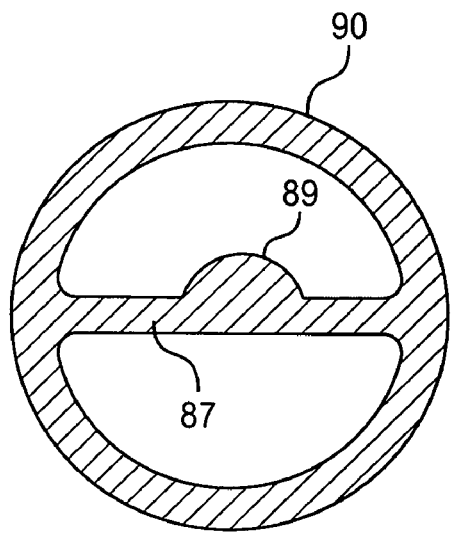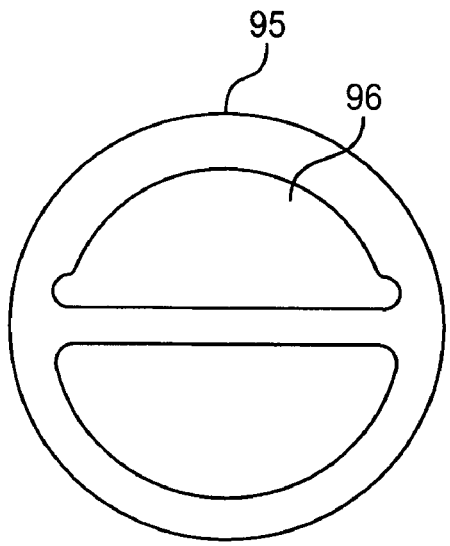
FIG. 8A  FIG. 8B
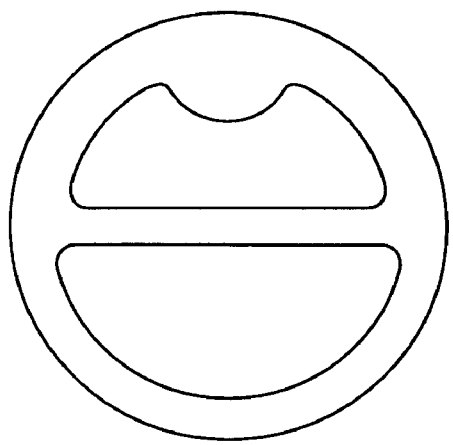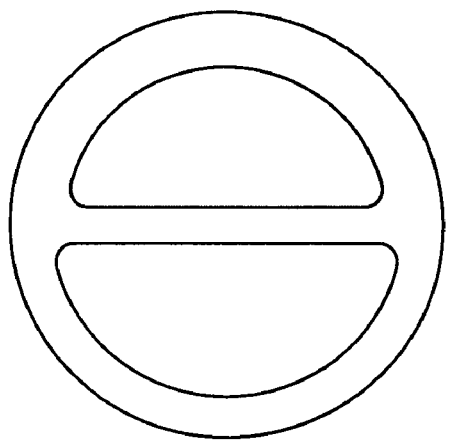
FIG. 8C  FIG. 8D

US 7,163,531 B2

USER-FRIENDLY CATHETER CONNECTION ADAPTERS FOR OPTIMIZED CONNECTION TO MULTIPLE LUMEN CATHETERS

FIELD OF THE INVENTION

The present invention relates in general to catheter connection adapters for connecting a dialysis patient to a source of dialysis fluid, and more particularly to catheter connection adapters that are designed to allow user-friendly access to peritoneal dialysis equipment utilizing a multiple lumen catheter such as a dual lumen catheter and that will ensure a secure and leak-free connection that can be manually connected after implantation of the catheter.

BACKGROUND OF THE INVENTION

Dialysis is a common treatment used to assist patients suffering from a wide variety of kidney problems including severe late stage renal insufficiency which usually results in total or near total kidney failure. This treatment cleans the blood and removes waste products and excess water from the body, a task normally performed by healthy kidneys. Presently, there are two main types of dialysis that are performed to compensate for kidney failure, namely hemodialysis and peritoneal dialysis.

In hemodialysis, the patient's blood is generally passed through a form of artificial kidney in order to cleanse it, followed by the return of the blood to the patient's bloodstream. In peritoneal dialysis, the patient's own peritoneum is used as a semi-permeable membrane in order to remove waste products, and this procedure is carried out by filling the peritoneal cavity with a dialysis solution, also known as dialysate, which preferably is introduced into the body via a permanently implanted catheter. In this process, waste products such as urea and creatinine, as well as excess water, pass from the blood through the peritoneum into the peritoneal dialysis solution, and after a given period of time, or dwell, the used dialysis solution or spent dialysate may be removed from the peritoneal cavity and then either discarded or purified for reuse. In general, the removal of the spent dialysate may be accomplished from a permanent catheter implanted in the body.

Due to the importance of the catheters in carrying out dialysis procedures, it is vitally important that the multiple connections involved in such processes be secure, leak-proof, properly aligned, and easily connectable. This is particularly important using certain catheters which need to be manually connected following implantation into a patient. In addition, since many of these devices are intended for use by a patient on an outpatient basis such as in the home without the supervision of a healthcare professional, it is important that the connections remain secure and in proper position so that there is no leakage or improper delivery of dialysis fluid. It is thus important that such connections be made as simple and effectively as possible so that secure and mistake-proof connections can readily be made manually following implantation of the catheter into a patient. Accordingly, there is a strong need to develop secure, user-friendly catheter connections and connection adapters which can be utilized with dialysis equipment including those units designed for home care on an outpatient basis.

Traditionally, dialysis systems have used catheters with a single lumen wherein the dialysis fluid is introduced into and removed from the patient via the same tube. However, more recently, many dialysis systems now employ multiple lumen catheters wherein it is possible to introduce dialysis fluid through at least one of the lumens and remove the spent dialysate through another lumen in the same catheter. An example of such a multiple lumen system is the dual lumen catheter disclosed in WO 02/30489, incorporated herein by reference, wherein a catheter is described in which dialysate flows through a first lumen into the patient and spent dialysate simultaneously flows out through a second lumen. Other multiple lumen catheters have been disclosed for example in patent references including U.S. Pat. Nos. 4,950, 259; 5,053,023; 5,167,623; 5,961,485; 5,868,717; 5,683, 640; 5,486,159; 5,480,380; 5,380,276; 5,188,593; 5,156, 592; 5,057,073; 5,009,636; 5,976,103; 5,961,486; 5,827, 237; 5,569,182; 5,221,255; 4,842,582; 4,623,327; and 5,346,471; PCT references WO 94/05363 and 96/29111; European Patent Application 333308; German Patent application 10042067; and Japanese Patent references 8-206216; 2-116380 and 1-303159; all of these patent references incorporated herein by reference.

Although these multiple lumen catheters may increase the efficiency of the dialysis process, they create additional problems with regard to the multiple connections between the dialysis equipment, the lumens of the catheter providing inflow and outflow, and the patient. With such multiple lumen systems, the need to create leak-proof and secure connections is even greater, and it is also important to make the systems mistake-proof and user-friendly so that the proper connections can be made easily and without confusion.

Accordingly, although numerous catheter connection systems are known, few of these even address the particular problems associated with multiple lumen catheter systems, and none provide solutions for obtaining user-friendly, secure, leak-proof connections for multi-lumen catheters such as those utilized in peritoneal dialysis systems. Examples of such prior systems include those disclosed in patent references including U.S. Pat. Nos. 6,113,572; 4,929, 236; 5,743,873; 5,129,891; 5,632,729; 5,399,165; 4,950, 255; 5,417,672; 6,190,349; 5,667,490; U.S. Pat. No. D431, 651; U.S. Pat. Nos. 5,190,529; 5,531,723; 4,781,185; 5,456, 676; U.S. Pat. No. D303712; U.S. Pat. Nos. 6,254,589; and 6,190,372; Japanese patent references 2000-0045999; 1-171499; and 8-269224; and European Patent EP 553254 B1; all of these patent references incorporated herein by reference, Another problem with catheters that are implanted in association with their utilization in peritoneal dialysis systems is that some of these catheters, such as the dual lumen catheter disclosed in WO 02/30489, have an implanted section which is made of a relatively hard material such as hard silicone so that they can maintain a proper configuration inside the peritoneal cavity when implanted. However, if such harder material is utilized in the part of the catheter that will be located external to the patient, it can create some discomfort for a patient. Although certain patents relate to catheters having a transitional area with an intermediate durometer, such as U.S. Pat. Nos. 6,135,992; 5,451,206; 5,348,536; 5,125,913; 5,792,124; and 4,739,768, all incorporated herein by reference, none have provided the necessary means whereby a multi-lumen catheter system can be simply and effectively made without such complex and difficult to manufacture materials, and yet provide the necessary internal durometer while maximizing comfort to the patient, being manually connectable, and providing a secure and leak-proof connection.

Further, other prior catheters utilized in procedures such as Continuous Flow Peritoneal Dialysis (CFPD) have had lumens which have a high interference with catheter connection adapter ports used to connect the patient to a source of dialysis fluid, and this makes connection even more difficult to accomplish.

Therefore, in addition to providing a connection assembly for multiple lumen catheters which is user-friendly and mistake-proof, so as to prevent the chance of an erroneous connection, it would be beneficial if the catheter used in connection with this assembly was more comfortable for the patient and could be connected easily with a minimum of resistance or interference.

Finally, in addition to providing a system of connections for multiple lumen catheters which can be made user-friendly and mistake-proof, it is also desirable to develop a system wherein the patient can stop or initiate the flow of dialysis fluid into or from the patient's peritoneal cavity, such as during the start or end of a dialysis procedure. Accordingly, it is also desirable to develop a user-friendly transfer set by which the user may easily and effectively set up the catheter tubing for dialysis and initiate or stop the flow of dialysis fluid when necessary during a dialysis operation involving a multiple lumen catheter.

Therefore, it is thus important to develop new catheters, catheter connection adapters and patient transfer sets which are user-friendly, mistake proof and which can provide secure and leak-proof connections, particularly for multiple lumen catheters containing at least two lumens, e.g., one for inflow and one for outflow, such as the implanted multiple lumen catheters employed for use in peritoneal dialysis systems.

SUMMARY OF THE INVENTION

Accordingly, it is thus an object of the present invention to provide catheter connection adapters which can provide leak-free, secure connections for multiple lumen catheters utilized in peritoneal dialysis systems.

It is another object of the present invention to provide catheter connection adapters which are user-friendly and mistake-proof and which can be readily connected manually after the catheter has been implanted into a patient.

It is further an object of the present invention to provide a method of performing peritoneal dialysis utilizing a catheter having at least two lumens, e.g., one for inflow and one for outflow, and to provide an improved connection adapter which allows for secure and leak-proof connections which are used in dialysis systems involving multiple lumen catheters which may be utilized by patients in a home setting.

It is a further object of the present invention to provide dialysis systems which can employ multiple lumen catheters which are easy to set up, connect and utilize, and which can afford maximum comfort and ease for the patient.

It is still further an object of the present invention to provide a dialysis system with connections which make the catheter easier for the user to connect and which allow the safe and effective use of a patient transfer set for use with a multiple lumen catheter which can be readily clamped and unclamped when appropriate by the patient.

It is even further an object of the present invention to provide connections for dual lumen catheters which have keyed internal configurations so that the connection between the multiple lumen catheter and the dialysis equipment can be made simple, user-friendly and mistake-proof for the person making the connections.

These and other objects are provided by virtue of the present invention which comprises a catheter connection adapter for use with multiple lumen catheters having at least two lumens, e.g., one for inflow and one for outflow, so that a continuous flow dialysis procedure can be carried out using a single catheter, and the catheter connection adapters of the invention contain features which allow a simple, secure and mistake-proof connection and which can be manually attached to the catheter after the catheter has been implanted into the dialysis patient. In particular, the catheter connection adapters of the present invention have been configured to contain ports which can be inserted into one end of the multiple lumen catheter, and the connection adapter of the invention is designed so that fluid from each of these ports is conveyed through the connection adapter to mating devices which connect it to other dialysis equipment. This connection adapter may comprise a single unit having two ports designed to fit into an implanted catheter emerging from the patient or may comprise two separate port connection adapters, each of which will fit inside one of the lumens of the multiple lumen catheter so as to connect the patient to a source of dialysis fluid via an inflow path, and to allow the spent dialysate coming from the patient to be sent via an outflow path to a drain or other fluid receptacle. In one of the preferred embodiments, a connection adapter is provided which has at least two ports and this connection adapter has a tapered gap between the ports which will be co-aligned with the multiple lumen catheter which permits an interference fit to be formed when the connection adapter ports of the invention are fitted into the catheter. In this embodiment, the gap between the connection adapter ports is tapered inward so that when the middle wall of the catheter, or catheter septum, slides into the gap or slit in the connection adapter, an interference fit is created between the connection adapter slit and the catheter septum which creates a leak-free seal and allows for the secure connection between the multiple lumen catheter and the dialysis equipment. Alternately, a connection adapter is provided wherein the ports which are introduced into the catheter are made to be flexible so that when the ports are inserted into the end of the catheter, the inner diameter of the catheter interferes with the outer diameter of the ports and presses them together. Additional compression may be added to further bring the ports together and provide a further seal around the catheter septum.

In additional embodiments, the catheter connection adapters of the present invention may be designed wherein the gap between the ports is offset so that the top and bottom ports are sized differently so as to be readily distinguished by the user and thus easily inserted in proper alignment with a multiple lumen catheter having the same offset and thus matching dimensions of the upper and lower lumens. Similarly, in the embodiment wherein the connection adapter comprises at least two ports which are not connected to each other, but which are designed to fit respectively into one of the lumens of an implanted multiple lumen catheter, these ports are also designed wherein the cross-section and/or size of one of the ports is different than the cross-section and/or size of the other port, and these ports will be designed to mate with a multiple lumen catheter which has at least one lumen, e.g., for inflow, sized and shaped to receive one of the ports, and at least one other lumen, e.g., for outflow, having a different size and/or cross-section which will be shaped to receive the second port.

In further embodiments, the connection adapters of the invention may also have a barbed end to further ensure proper alignment and secure connection between the catheter and the connection adapter. Similarly, an improvement to allow a simultaneous, mistake-proof connection between an implanted multiple lumen catheter and the catheter connection adapter of the invention is accomplished by having the catheter lumens and the connection adapter ports be geometrically keyed to fit exclusively with each other in lock and key manner when in the proper alignment. This may be accomplished whether both ports are part of one connection adapter element or where the ports are separate. These specific geometric shapes may take on a variety of forms, e.g., oblong shapes, particular notches, etc., and in all cases the configuration of the ports is designed to match the configuration of the multiple lumen catheter in such a way as to ensure that the proper alignment and configuration is achieved. These geometrically specific designs with special lock and key features help ensure the safety, efficacy and proper functioning of continuous flow peritoneal dialysis that may be performed using the catheters, catheter connection adapters and transfer sets of the present invention.

These embodiments and other alternatives and modifications within the spirit and scope of the disclosed invention are described in, or will become readily apparent from, reference to the detailed description of the preferred embodiments provided herein below.

BRIEF DESCRIPTION OF THE DRAWING FIGURES

FIG. 8A is a cross-sectional view of a dual lumen catheter that has been designed to match the configuration of the ports of a connection adapter in accordance with the present invention.

FIG. 8B is a cross-sectional view of a alternative dual lumen catheter that has been designed to match the configuration of the ports of a connection adapter in accordance with the present invention.

FIG. 8C is a cross-sectional view of a alternative dual lumen catheter that has been designed to match the configuration of the ports of a connection adapter in accordance with the present invention.

FIG. 8D is a cross-sectional view of a alternative dual lumen catheter that has been designed to match the configuration of the ports of a connection adapter in accordance with the present invention.

DETAILED DESCRIPTION OF THE PREFERRED EMBODIMENTS

Figure 1:
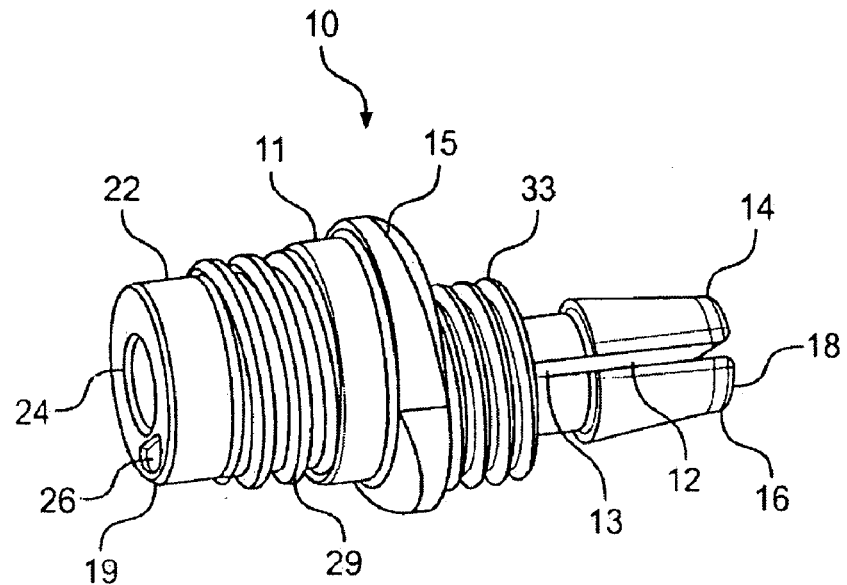
FIG. 1 is a perspective view of a catheter connection adapter in accordance with the present invention.

As shown in the drawing figures appended hereto and as described in the specification below, in accordance with the present invention, there is provided a catheter connection adapter 10 which is capable of providing a secure, user-friendly and mistake-proof connection between a multiple lumen catheter and other dialysis equipment through which fluid will flow during a dialysis operation. In accordance with the invention, the multiple lumen catheter utilized with the connection adapter of the invention will have at least two lumens, e.g., one for inflow and one for outflow, and while the description below refers to a preferred embodiment wherein the connection adapter is designed to be used with a dual lumen catheter, it is understood that connection adapters of the invention could be configured for catheters with additional lumens. In accordance with the invention, the connection adapter 10 of the invention will have particular features to allow a secure and properly aligned connection between a multiple lumen catheter such as one which is implanted in a patient for purposes of peritoneal dialysis and to the source of dialysis fluid and/or a means which receives spent dialysate from the patient's peritoneal cavity. As will be discussed below, the connection adapter of the invention is shown as a single unit having at least two ports, but it is also contemplated that the invention comprises at least two individual ports which may be separate from each other, but which maintain the cross-section and/or size of the upper and lower ports, respectively, as described hereinbelow as part of a single connection adapter unit.

In accordance with the present invention, such as observed in FIG. 1, a connection adapter 10 may be provided which has at least two ports 14 and 16, and which also features tapering of the gap 12 between ports 14 and 16 of the connection adapter 10. In addition, the present connection adapter 10 may also have flexible ports which can be brought together when inserted into a multiple lumen catheter such as dual lumen catheter 20. Even further, as described below, the connection adapter of the invention may be constructed with particular configurations of the shape of the ports which mate in lock and key fashion with similarly shaped dual lumen catheters so as to provide a mistake-proof connection wherein the ports can only be inserted in the catheter in proper alignment and position.

As observed for example in the embodiment depicted in FIG. 1, the catheter connection adapter 10 of the present invention is comprised of a housing 11 which is generally cylindrical and which has two ports 14 and 16 at one end of the housing. As shown in the drawing figures, ports 14 and 16 are designed to be inserted into a dual lumen catheter 20 with each port designed to fit into a particular lumen of the catheter. In the preferred embodiment of the invention, the ports are separated from each other by gap 12, and the connection adapter 10 is generally configured so that the ports will be inserted into a dual lumen catheter 20 such that the middle wall or septum 17 of the catheter will fit into the gap 12 between the ports when the ports are inserted into the lumen of the catheter. In this fashion, a tight fit is provided so that fluid from one of the lumens of the catheter, whether inflow or outflow, will be conducted in a leak-free manner to the corresponding port of connection adapter 10, and the fluid in the other lumen of the catheter will likewise be constrained to flow only through the corresponding port in the connection adapter. In this manner, the dual lumen catheter may effectively be used in peritoneal dialysis and the proper flow is maintained in a leak-free manner. Another feature of the connection adapter of the present invention is that it can be manually attached which is important since the catheters utilized with the connection adapters can only be connected after implantation into a patient. Accordingly, it is necessary to provide a quick, simple and mistake-proof connection so that the catheter may be connected to a source of dialysis fluid in proper alignment for conducting a dialysis procedure.

As shown in FIG. 1, the preferred catheter connection adapter 10 of the invention is comprised of ports 14 and 16 which extend from a central portion 15 in housing 11 which sits between ends of the connection adapter. As shown for example in FIG. 2, the gap 12 is designed to receive septum 17 of dual lumen catheter 20, and the gap preferably ends at the side of central portion 15 of connection adapter 10 which faces port end 18. In the preferred embodiment, as described further below, the port end may be adapted to have threading 33 disposed on the central projection 15 and facing end 18 in order to fit a threaded sleeve which may be placed over the ports to assist in sealing the connection after it is made. In this embodiment, the gap 12 preferably ends at point 13 which is at the end of threading 33. In addition, as described above, at one end 18 of the connection adapter 10 are the ports for insertion into the dual lumen catheter, and at the other end 19 which faces the opposite direction from the port end is a generally cylindrical projection 22 which is capable of mating with a device for transferring fluid into and out of said housing. Such a device, or transfer set, is disclosed, for example, in co-pending U.S. patent application Ser. No. 10/222,968 to Seese et al., incorporated herein by reference. In the preferred embodiment of the present invention, the connection adapter 10 is designed so that fluid paths will be created between the ports 14 and 16 and the cylindrical projection 22 at mating end 19 so that the fluid coming from or going to a particular lumen of the dual lumen of the catheter 20 will be channeled properly and will be kept separate from the adjoining lumen. Accordingly, the cylindrical projection 22 contains fluid paths 24 and 26 which are aligned respectively with said ports 14 and 16 so that fluid passing through each of said ports will flow properly and separately through the connection adapter and either into or out of the catheter 20. In the preferred embodiment, the cylindrical projection is threaded to allow a mating device which transfers fluid from the connection adapter to be screwed onto the connection adapter to afford a tight fit. In the preferred case, these threads 29 are added at the side of central portion 15 which faces towards the end having the cylindrical projection as shown in FIG. 1 and will be configured so that the connection adapter and catheter will be in proper position following complete threading onto projection 22.

In the general operation of the present invention, the ports 14 and 16 of connection adapter 10 will be inserted at the open end 21 of dual lumen catheter 20, such as the end of the catheter that is coming out of a patient. This catheter can be any suitable catheter having at least two lumens, such as the dual lumen catheter shown and described in PCT patent reference WO 02/30489, or the multiple lumen catheters described in co-pending U.S. patent application Ser. No. 10/222,968 to Seese et al., both of these patent applications incorporated herein by reference. In the present invention, as shown for example in FIG. 2, the connection adapter 10 is designed so that port 14 fits snugly into upper lumen 23 of catheter 20, and port 16 fits snugly into lower lumen 25 of catheter 20. In this manner, the connection adapter of the invention provides a means by which both lumens of catheter 20 can be connected to a source of dialysis fluid as well as to a suitable receptacle which will receive the spent dialysate from the patient and either discard it or further direct it to means to recycle or regenerate the spent dialysate. As described above, the connection adapter or connection adapter 10 of the present invention is provided with channels or pathways from the ports 14 and 16, respectively, back through central portion 15 and through fluid paths 24 and 26, respectively, in the cylindrical projection 22 at the end of housing 11 opposite from the ports. In this manner, a fluid channel is provided for incoming dialysis fluid, such as through upper fluid path 24, upper port 14 and upper lumen 23 of catheter 20, as well as for spent dialysate returning from the dialysis patient which may flow through lower lumen 25, connection adapter port 16 and out through lower fluid path 26 of connection adapter 10, or vice versa. The connection adapter of the present invention is preferably manufactured of any suitable rigid, chemical and creep resistant plastic which should also be lightweight yet sturdy, sterilizable and injection moldable. Any of a number of commercially available plastics are suitable for use in the present invention including polycarbonate, polyurethane, or other suitable hard plastic.

Figure 3:
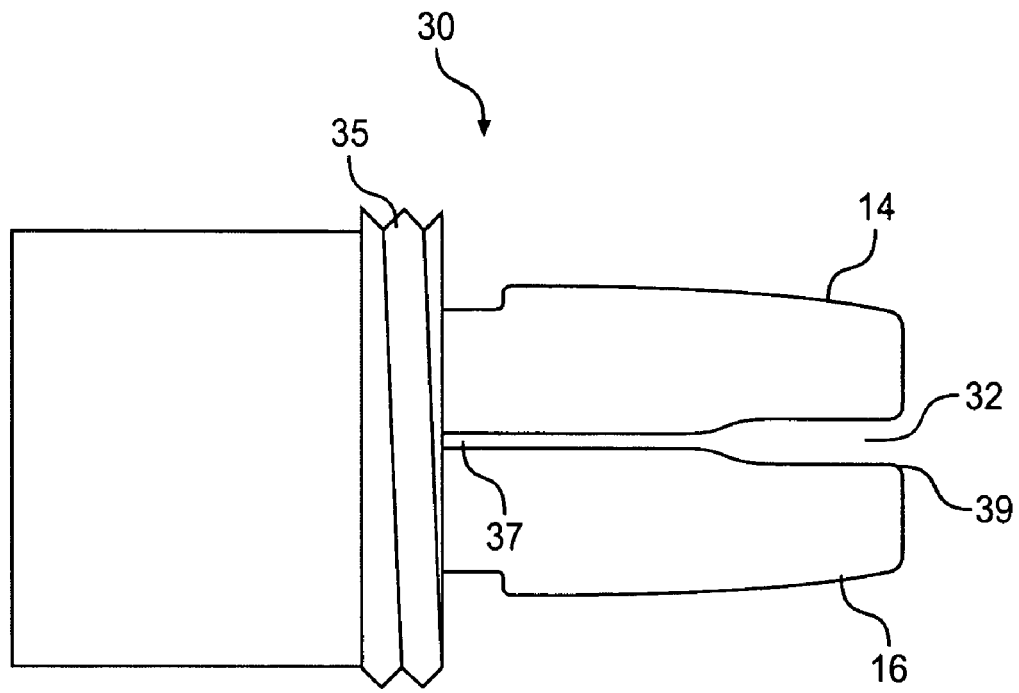
FIG. 3 is a side view of an alternative embodiment of the connection adapter of the present invention.

In accordance with the present invention, the connection adapter 10 of the present invention may be provided with additional means to ensure a snug and leak-proof interference fit or seal between the catheter 20 and the connection adapter 10, and additionally, other features may be employed to ensure that the patient may readily and without confusion hook up the catheter to the connection adapter properly so as to maintain proper alignment and correct flow of the dialysis fluid into and out of the patient. In one preferred embodiment of the invention, as shown in FIG. 3, a snug interference fit or seal between connection adapter 30 and the dual lumen catheter 20 is provided by virtue of a tapered gap 32 between ports 14 and 16 in which the width of gap 32 is larger at the outer end 39 between the ports than it is at the inner end 37 of the gap closer to central region 35 of connection adapter 30, although the opposite embodiment wherein the gap is smaller at the outer end is also possible. In this embodiment using the tapered gap, an interference fit is created between the catheter connection adapter 30 and the septum 17 of dual lumen catheter 20 as the septum 17 slides into the gap 32 when the connection adapter ports 14 and 16 are inserted into their respective lumens 23 and 25 in dual lumen catheter 20. Because the gap 32 is tapered, it creates an interference fit between the connection adapter 30 and the septum 17 of the catheter 20 and thus creates a snug seal between the catheter and the connection adapter of the invention.

Figure 4:
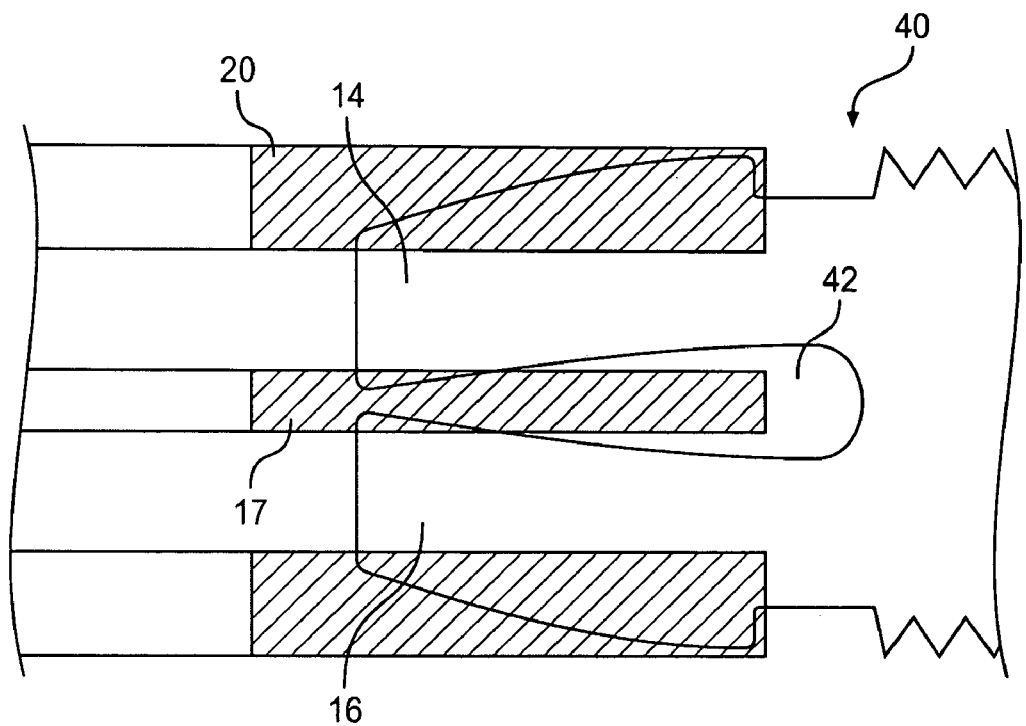
FIG. 4 is a side view of an alternative embodiment of the connection adapter of the present invention.
Figure 5:
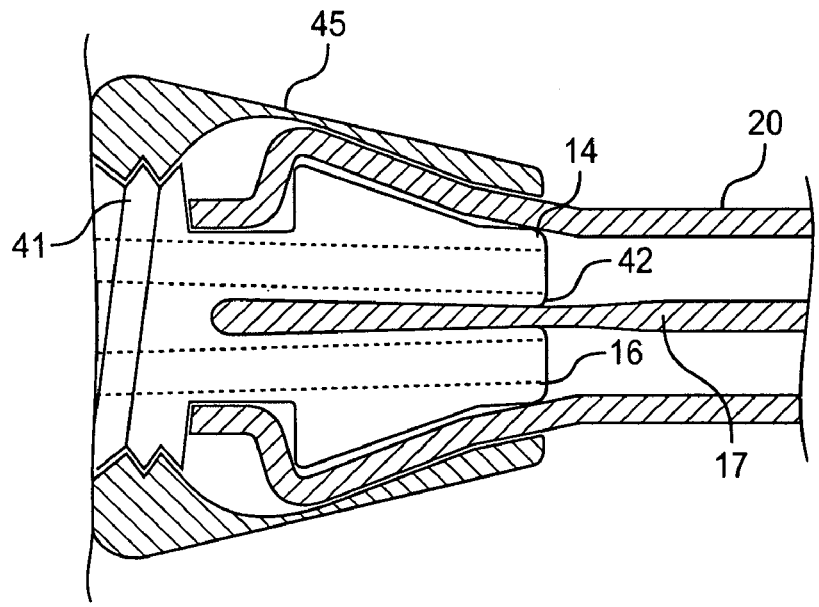
FIG. 5 is a side, partially cross-sectional view of the embodiment of FIG. 4 in combination with a compression sleeve.

In another embodiment of the present invention, the ports 14 and 16 are made to be flexible so that they may be brought together when inserted into the dual lumen catheter 20. In this embodiment, it is preferred that the connection adapter be made of a flexible material such as a plastic with a high elastic modulus. As shown in FIG. 4, in this embodiment, the gap 42 of connection adapter 40 is narrowed when inserted into dual lumen catheter 20 because the inner diameter of the catheter will interfere with the outer diameter of the ports thus compressing them together. Once again, in this embodiment, the connection adapter 40 is sized to be compatible with the dual lumen catheter and thus the gap 42 will be positioned so as to properly received the septum 17 of catheter 20, and the ports 14 and 16 of connection adapter 40 will be compressed onto the septum 17 when the ports are inserted into catheter 20. In an additional embodiment as shown in FIG. 5, it may also be possible to add a compression sleeve 45 which fits around the catheter 20 and the connection adapter 40 so as to exert further compression on the outer surface of the catheter over the ports. This compression acts to bring ports 14 and 16 even closer than by the catheter alone. Once again, with the added compression from sleeve 45, the gap 42 between the ports narrows in width around septum 17, and an interference fit is created thus forming a seal between the catheter septum 17 and the connection adapter gap 42. In the desired operation, a compression sleeve 45 may be placed around the dual lumen catheter 20 prior to the insertion of the catheter into the connection adapter 40. Then, after the ports are inserted into the catheter, the compression sleeve may be brought over the catheter at the end wherein the ports are inserted, and the compression sleeve acts to further compress the ports together as described above. In a particularly preferred embodiment, the connection adapter 40 is manufactured with screw threads 41 on the side of the central portion facing the port end as shown in FIG. 5, and thus the compression sleeve preferably screws onto the connection adapter to achieve proper compression and positioning. If it is desired to undo the connection, the compression sleeve may be unscrewed and the ports removed from the catheter.

Figure 2:
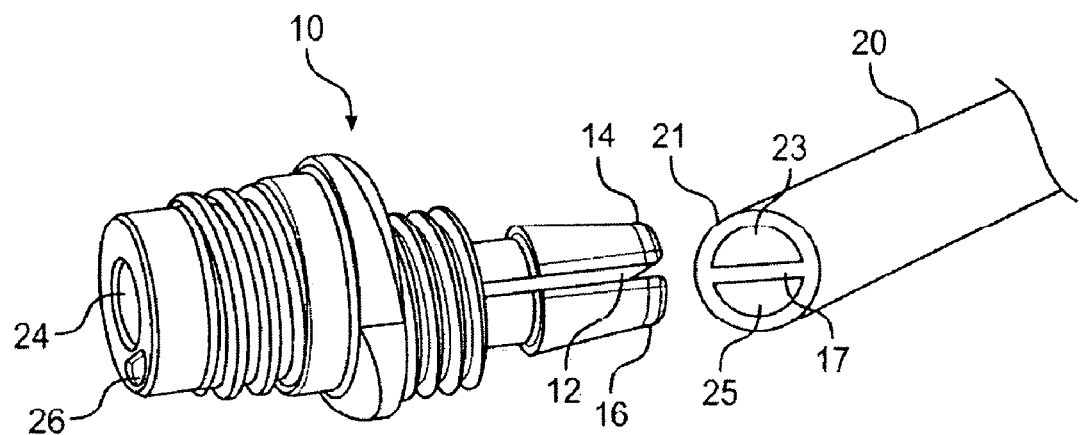
FIG. 2 is a perspective view of the connection adapter of FIG. 1 in combination with a dual lumen catheter in accordance with the present invention.

In the preferred embodiments of the present invention, the connection adapter ports 14 and 16 are sized and shaped so as to snugly fit into a dual lumen catheter which has an upper and lower lumen sized and shaped to receive the connection adapter ports of the invention. In one embodiment of the invention, the ports have a "Double-D" shape as best observed in FIG. 2, and in this embodiment, the ports form a back-to-back double D wherein the internal shapes of the ports are of the same size and are symmetrical. This port design will fit snugly into a catheter which has the same symmetrical double-D configuration as shown in FIG. 2. In the catheter shown in FIG. 2, the septum or middle wall 17 is disposed in the center of the catheter such that the two double-D lumens are symmetrical and are of the same size.

Figure 6:
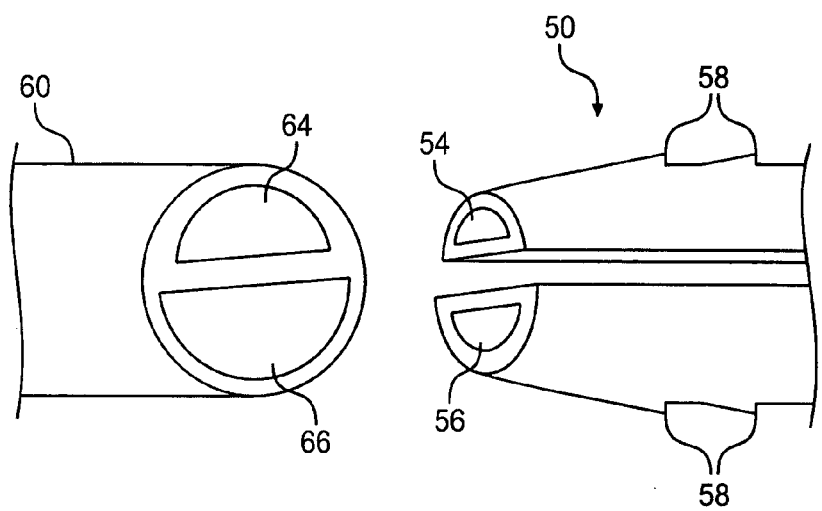
FIG. 6 is a perspective view of an alternative embodiment of a connection adapter in accordance with the invention alongside a matching dual lumen catheter.

However, in an alternate embodiment in accordance with the present invention, the middle wall or septum 17 is offset from the center, as shown in FIG. 6, which results in an asymmetric double-D pattern wherein one of the ports is smaller and one of the ports is larger. As shown in FIG. 6, in this-embodiment, the connection adapter 50 has a smaller upper port 54 and a larger lower port 56 which fit, respectively, into upper lumen 64 and lower lumen 66, respectively. In accordance with the invention, the asymmetrical pattern of cross-sections for the upper and lower ports provides a means whereby the proper positioning and alignment of the connection adapter and catheter of the invention can take place because with a different upper and lower section, the connection adapter ports will only fit one way into the multiple lumen catheter used in accordance with the invention. Accordingly, the asymmetric nature of this embodiment will once again provide a user-friendly means of indicating the proper configuration for connecting the catheter to the connection adapter in accordance with the invention. As an additional means to ensure a secure and leak-proof connection using the connection adapter of the invention, the connection adapter 50 of the invention may contain one or more barbed slits 58 on either or both ports in order to further help seal the connection adapter to the catheter.

Figure 7:
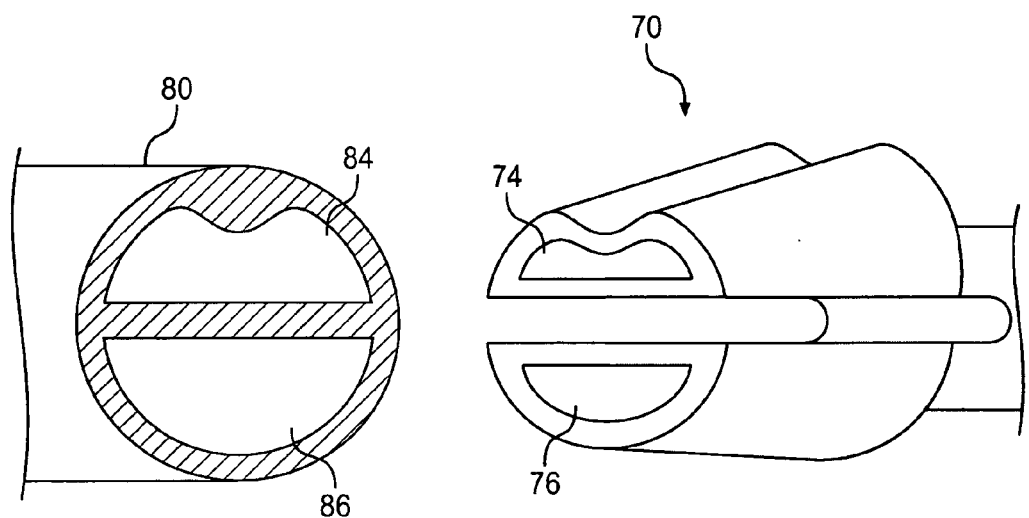
FIG. 7 is a perspective view of an alternative embodiment of a connection adapter in accordance with the invention alongside a matching dual lumen catheter.

In a further embodiment in accordance with the present invention, the connection adapter is designed with ports having a specific geometric shape that is keyed to a shape of the lumens of the multiple lumen catheter in unique lock-and-key fashion. In this manner, once again the catheter and connection adapter are made mistake-proof since the ports of the connection adapter can only be placed into the dual lumen catheter in the specific manner wherein the outer shape of the ports matches the internal cross-section of the lumens of the catheter, and this ensures proper alignment and positioning of the connection adapter and catheter so that a safe and effective peritoneal dialysis procedure to take place. As shown in FIGS. 7 and 8A–8D, this embodiment can take on a variety of different port shapes, in each case the shape of the ports corresponding to matching shapes in the multiple lumen catheter so as to receive the port of the unique geometrical configuration in such a position which ensures proper alignment and functioning of the peritoneal dialysis system. For example, as shown in FIG. 7, the connection adapter 70 of the invention has a lower port 76 having the D-shaped as shown in embodiments described above, but wherein the upper port 74 has a unique configuration featuring a generally U-shaped depression or notch at the top central portion of the upper port. In accordance with the invention, this particular shape of the ports will be matched in the dual lumen catheter of the invention wherein the internal cross-section of the upper lumen 84 has the same shape as the outer surface of the upper port 74 so as to allow the connection adapter to be inserted properly in the catheter. Similarly, as also shown in FIG. 7, the lower lumen 86 of catheter 80 is sized to match with the lower port 76 of connection adapter 70. As shown for example in the drawing FIGS. 8A–8D, numerous alternative designs are possible, including a configuration wherein the upper lumen of the catheter has a notch or projection 89 on the upper surface of the septum or middle wall 87 of catheter 90, as shown in FIG. 8A. Alternatively, a catheter 95 is shown in FIG. 8B which has a roughly bell-shaped upper lumen 96 which will match up with a similarly-sized and shaped the upper port of an connection adapter (not shown) in accordance with the invention. Still other designs for the cross-section of the lumens of dual-lumen catheters which will match up with similarly sized and shaped ports in the connection adapters of the invention are shown in FIGS. 8C and 8D.

Figure 9:
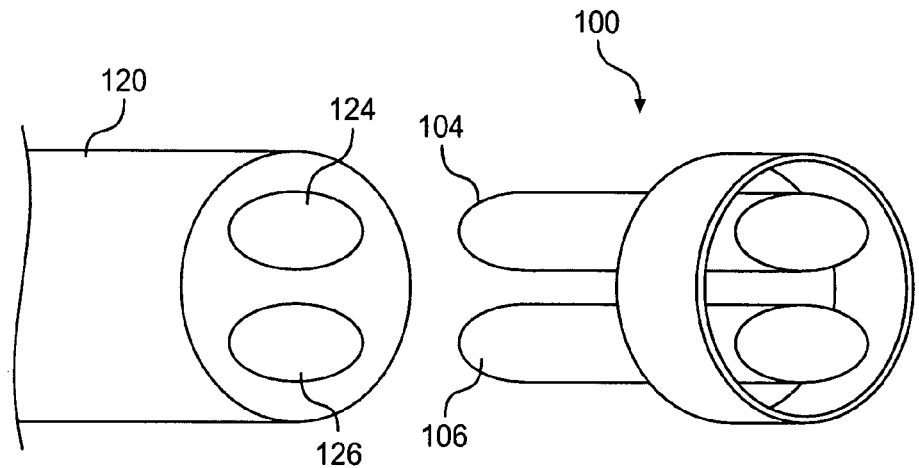
FIG. 9 is a perspective view of an alternative embodiment of a connection adapter in accordance with the invention alongside a matching dual lumen catheter.
Figure 10:
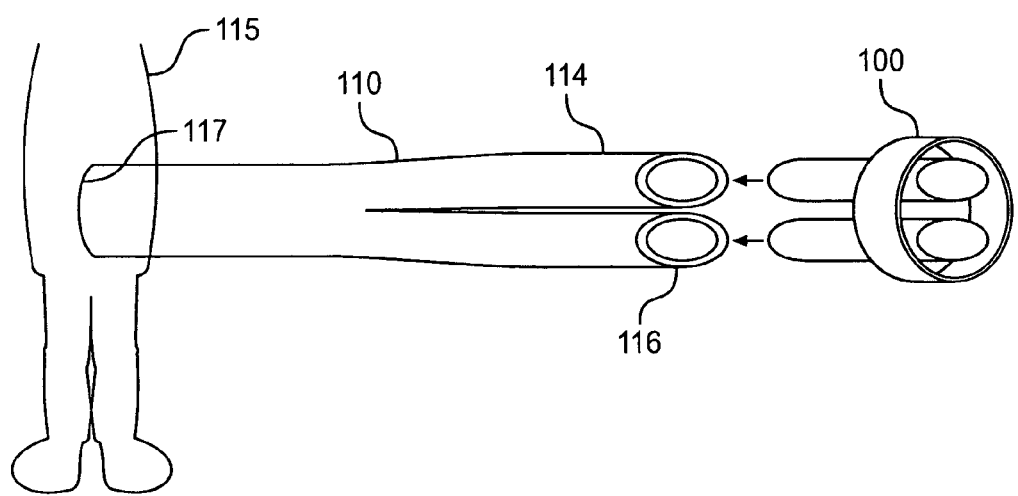
FIG. 10 is a perspective view of the connection adapter as shown in FIG. 9 alongside an alternative embodiment of a catheter as implanted in a patient.

In still another embodiment in accordance with the present invention, the connection adapter may be configured so that the ports may have any of a wide range of other suitable shapes which will match up with similarly sized and shaped catheter lumens. For example, in the embodiment shown in FIG. 9, each port has an oval shape, and once again, this embodiment is designed to match up with a multiple lumen catheter having at least two lumens which will have a matching oval shape. In this embodiment, as shown in FIG. 9, the catheter connection adapter 100 of the present invention has an upper port 104 and a lower port 106 which fit, respectively, into oval-shaped upper lumen 124 and lower lumen 126 on catheter 120. In another embodiment, the catheter connection adapter 100 may be inserted into a catheter such as shown in FIG. 10, wherein catheter 110 has split oval tubes 116 and 114, but wherein these tubes have been split off a catheter having a single outer diameter which emerges from the patient site 117 from patient shown generally at 115. Still other shapes of the connection adapter ports and catheter lumens are possible, including round, semi-circular, triangular, etc.

As indicated above, in the preferred modes of the invention, the connection adapter 10 will be constructed so as to be connectable to a transfer device through which the patient is connected to a source of dialysis fluid, and it is necessary to ensure that the connection adapter connection to this device be designed so that the lumens of the catheter line up properly to ensure correct flow of the dialysis fluid. In this regard, it is possible for he connection adapter 10 to have threads 29 extending from the side of the central projection facing the end 19 of the connection adapter away from ports 14 and 16, as observed in FIG. 1. In this embodiment, a centrally located lumen 24 will match up with the upper lumen 23 of the catheter 20, and a second opening 26 in the connection adapter 10 will be on the periphery of central projection 22 which, when the connection adapter is screwed into a transfer device will be designed to end up in the proper position to receive or transfer fluid coming from the lower lumen 25 of catheter 20.

Figure 11:
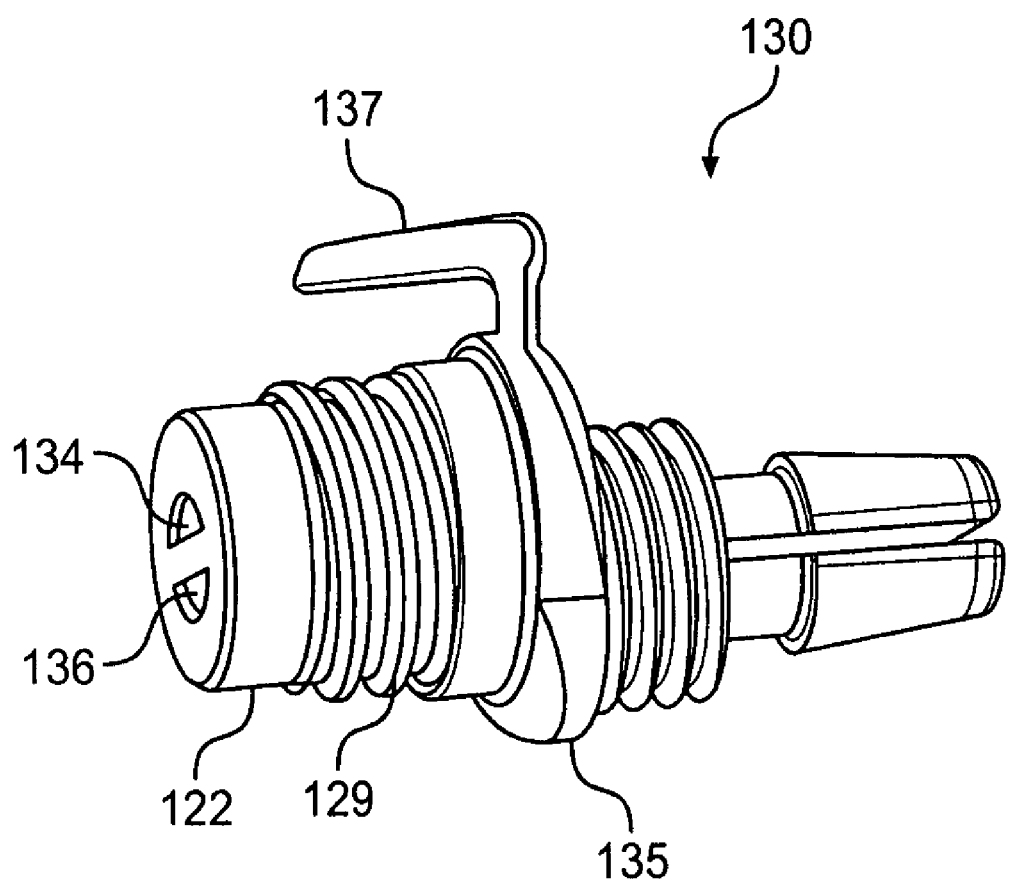
FIG. 11 is a perspective view of an alternate embodiment of the catheter connection adapter in accordance with the present invention.

In a second embodiment, as shown in FIG. 11, an connection adapter 130 in accordance with the invention is modified with regard to the end away from the ports which will be connected to a transfer set connection adapter (not shown), and in this case the cylindrical projection 122 has a double-D configuration including upper lumen 134 and 136. The connection adapter also has threading 129 located on the side of central region 135 facing the cylindrical projection 122. In order to ensure that the double-D configuration is secured in proper position when the connection adapter 130 is connected to a suitable transfer device, a stationing arm 137 is also provided which extends from the central region and which will mate with an appropriate slot in a transfer device which will be screwed onto the cylindrical projection end of connection adapter 130. In this manner, when the transfer set connection adapter has been screwed on properly onto the connection adapter 130, the arm will fit in the slot at the top part of the transfer connection adapter and lock the connection in place with the dual lumens in proper position. In an alternate embodiment, the catheter connection adapter such as connection adapter 130 having a double-D configuration on cylindrical projection 122 may be made without threading, and in this case, a suitable mating transfer set connection adapter is simply placed onto the connection adapter 130 to achieve the connection, and the transfer set connection adapter preferably contains a groove so that a compression sleeve with a notch fitting that groove can be brought over the connection when made and screwed in place to further secure the connection in proper position.

Accordingly, the catheter connection adapters of the present invention can be utilized with multiple lumen catheters to allow safe, effective and properly positioned and aligned peritoneal dialysis to take place, either in a clinical setting or in the home wherein a patient learns to perform the dialysis procedure without the aid of a healthcare professional. These multiple lumen catheters may include the dual lumen catheters such as described above or in WO 02/30489, or these may include catheters having more than two lumens in a variety of configurations, including those where the three lumens are divided equally in shape, or those catheters wherein a third lumen runs through the middle wall of a catheter having an upper and lower lumens. Many such multiple lumen catheters are shown in the prior art references described above. In accordance with the invention, a multiple lumen catheter can be connected using the connection adapters of the invention following implantation of the catheter into the patient, and this connection is utilized in conjunction with other devices, such as a transfer set, whereby the patient can link up the catheter to a source of dialysis fluid. In the common case, a dialysis patient will have previously been fitted with an implanted catheter suitable for use in a dialysis operation wherein one end is implanted in the patient, and the other end emerges from the patient and provides a site whereby the peritoneal cavity of the patient may be hooked up to the source of dialysis fluid. In this regard, as described above, the connection adapter of the invention may be threaded so that a transfer set device may be simply and securely screwed onto the connection adapter with a simple twist connection which is configured to end up in the proper position for the transfer of fluid through the dual lumen catheter. Other features may be employed to further ensure a tight fit between the catheter connection adapter and the transfer set such as an arm/slot arrangement wherein a rigid arm on the catheter connection adapter of the invention fits into a slot in the transfer set to help lock the connection and prevent disconnection. Further, the connection adapters of the invention may be designed as single units containing at least two ports for use with multiple lumen catheters having at least two ports, but in addition, the ports having the features as described above may be used separately from a single unit, but instead each port will be attached directly to a lumen of a multiple lumen catheter. In these cases, these separate ports will have a port end which will fit into the lumen of the catheter and will have an opposite end that will be connectable to either a source of dialysis fluid (for inflow) or a drain or other fluid receptacle (for outflow).

In summary, through the use of the connection adapters of the present invention, a dialysis system is provided with safe, mistake-proof and leak-proof connections between an implanted multiple-lumen catheter and a source of dialysis fluid, and this system will allow an effective dialysis procedure to be carried out by a patient on an outpatient basis with the proper connections to ensure correct inflow and outflow of the dialysis fluid.

The present invention has been described above with regard to exemplary embodiments, but as will be understood by those of ordinary skill in the art, the present invention encompasses numerous additional embodiments which will fall within its scope in addition to the specific embodiments described above.

What is claimed is:

1. A catheter connection adapter configured for use with a multiple lumen catheter, the adapter comprising:
   a generally cylindrical housing having a port connector and a mating connector disposed distal to the port connector, the port connector including:
   a first port having a first cross-section, the first port configured to engage a first lumen formed within the multiple lumen catheter; and
   a second port having a second cross-section that is different from the first cross-section, the second port formed adjacent to the first port and configured to engage a second lumen formed within the multiple lumen catheter;
   wherein the mating connector fluidly and via a plurality of threads couples the generally cylindrical housing to a fluid transfer device to promote fluid transfer into and out of the first and second ports and the first and second lumens of the multiple lumen catheter.

2. The adapter of claim 1, wherein the first and second ports cooperate to define a gap sized to engage a septum formed between the first and second lumens of the multiple lumen catheter.

3. The adapter of claim 2, wherein the gap is a tapered gap having a first dimension adjacent a central portion of the generally cylindrical housing and a second dimension distal to the central portion, wherein the second dimension is greater than the first dimension.

4. The adapter of claim 3, wherein the mating connector adjacent to the central portion includes a plurality of threads formed along an outer diameter of the mating connector.

5. The adapter of claim 3, wherein port connector adjacent to the central portion includes a plurality of threads formed along an outer diameter arranged to engage a compression device positioned along an outer diameter of the multiple lumen catheter.

6. The adapter of claim 1, wherein the first and second ports are each flexible ports configured to deformably engage the first and second lumens of a multiple lumen catheter.

7. The adapter of claim 6, further comprising a compressing device slideably engaging an outer diameter of the multiple lumen catheter, the compression device configured to engage the first and second ports when the ports are cooperating with the first and second lumen of the multiple lumen catheter.

8. The adapter of claim 1, wherein the generally cylindrical housing includes a threaded central portion sized to engage a compression device adjacent to the port connector.

9. The adapter of claim 1, wherein the first cross-section is a keyed geometric profile configuration that cooperates with a mating geometric profile formed in the first lumen of the multiple lumen catheter.

10. The adapter of claim 9, wherein the keyed geometric profile defines a notch formed within an outer surface of the first port, the notch sized to carry a projection formed along the first lumen of the multiple lumen catheter.

11. The adapter of claim 9 wherein the keyed geometric profile defines an at least substantially U-shaped notch formed with an outer surface of the first port, the U-shaped notch sized to carry a matching projection formed along the first lumen of the multiple lumen catheter.

12. The adapter of claim 1, wherein first and second cross-sections of the first and second ports each define an at least substantially oval cross-section.

13. The adapter of claim 1, wherein first and second cross-sections of the first and second ports each define an at least substantially double-D cross-section.

14. The adapter of claim 13, wherein the first port is of a different size than the second port.

15. The adapter of claim 1 further comprising at least one barb formed along an outer surface of the first port.

16. A catheter connection adapter configured to provide a connection between a multiple lumen catheter and a transfer device through which dialysate fluid flows, the adapter comprising:
   a generally cylindrical housing having a central portion;
   a mating end formed adjacent to the central portion of the generally cylindrical housing and including a plurality of threads for connecting to the fluid transfer device;
   first and second ports formed adjacent to the central portion and distal to the mating end, wherein the first and second ports cooperate to define a gap; and
   wherein the first port is formed with a first geometric shape sized for insertion within a complimentary lumen of the multiple lumen catheter and the second port is formed with a second geometric shape that is different than the first geometric shape, the second geometric shape sized for insertion within a second complimentary lumen of the multiple lumen catheter.

17. The adapter of claim 16, wherein the first and second ports cooperate to define a substantially cylindrical cross-section sized to engage the first and second lumens formed within the multiple lumen catheter.

18. The adapter of claim 16, wherein the first port includes a notch formed on an outer surface, the notch sized to engage a projection formed along an inner surface of the multiple lumen catheter.

19. The adapter of claim 16, wherein the first port includes an at least substantially U-shaped notch formed on an outer surface, the notch sized to engage a rounded projection formed along an inner surface of the multiple lumen catheter.

20. A catheter connection adapter configured to provide a fluid connection between a multiple lumen catheter and a transfer device through which fluid flows, the adapter comprising:
   a generally cylindrical housing;
   at least two ports each having a unique cross-section located on a first end of the housing, each of the at least two ports configured for insertion into a lumen having a complimentary cross-section formed within the multiple lumen catheter, and wherein each of the at least two ports is configured to conduct fluid into or out of the lumen of the multiple lumen catheter into which it is inserted, and wherein the multiple lumen catheter is fluidly coupled to the transfer device, such that fluid flowing through one of the at least two ports can be directed into a patient fluidly coupled to the fluid transfer device, and fluid from the other of said at least one port can be directed out of the patient; and
   a threaded connector located on a second end of the housing for fluidly coupling the multiple lumen, catheter to the transfer device.

21. The adapter of claim 20, wherein one of the at least two ports includes a keyed geometric shape configured to match a mating geometric shape of the corresponding lumen formed within the multiple lumen catheter.

22. The adapter of claim 20, wherein one of the at least two ports includes a notch configured to mate with a corresponding projection formed on one of the lumen formed within the multiple lumen catheter.

23. The adapter of claim 20, wherein the ports have different shapes so that one port can only be inserted into a matching inflow lumen of the multiple lumen catheter, and the other port can only be inserted into a matching outflow lumen of the multiple lumen catheter.

* * * * *